(12) United States Patent
Noda et al.

(10) Patent No.: US 7,544,516 B2
(45) Date of Patent: Jun. 9, 2009

(54) REAGENT FOR DETERMINATION OF CALCIUM AND DETERMINATION METHOD

(75) Inventors: Kenta Noda, Koriyama (JP); Ryo Kojima, Koriyama (JP); Katsuhiro Katayama, Koriyama (JP)

(73) Assignee: Nitto Boseki Co., Ltd., Fukushima-Shi (JP)

( * ) Notice: Subject to any disclaimer, the term of this patent is extended or adjusted under 35 U.S.C. 154(b) by 777 days.

(21) Appl. No.: 11/169,749

(22) Filed: Jun. 30, 2005

(65) Prior Publication Data

US 2006/0008915 A1      Jan. 12, 2006

(30) Foreign Application Priority Data

Jul. 8, 2004    (JP)    ............................. 2004-201331

(51) Int. Cl.
*G01N 30/74*  (2006.01)

(52) U.S. Cl. ........................................ 436/79; 436/166

(58) Field of Classification Search ................... 436/79, 436/166

See application file for complete search history.

(56) References Cited

U.S. PATENT DOCUMENTS 3,934,977 A *  1/1976  Cleaver .................... 436/74
5,482,866 A     1/1996  Denton et al. ............. 436/79

FOREIGN PATENT DOCUMENTS

| JP | 54-36996 | 3/1979 |
| JP | 02-31616 | * 2/1990 |
| JP | 4-120464 | 4/1992 |
| JP | 6-50976 | 2/1994 |
| JP | 6-505560 | 6/1994 |

OTHER PUBLICATIONS

European Search Report dated Jun. 19, 2007.*

Lizhong et al. "Studies on the Chromogenic Reaction of Mixed Surfactant System Vanadium (IV)—Chlorophosphonazo III-CTMAB-Emulsifier OP and its Application" Journal of Zhejiang Institute of Technology 1991, 1, 54-59.*

Medda et al. "The Vanadate Complex of teh Calcium-Transport ATPase of teh Sarcoplasmic reticulum, its Formation and Dissolution" European Journal of Biochemistry 1983, 137, 7-14.*

Qureshi, "The Spectrophotometric Determination of Calcium (II) in Steel Making Alloys". Pakistan Journal of Science (1979), 31(3-6), 212-14.*

Zagidullina et al. "Spectrophotometric Determination of the Acetic Acid Content", Kemerovski Technological Institute of the Food Industry, Nos. 1-3, 1991, p. 230.*

Lizhong et al. "Studies on the Chromogenic Reaction of Mixed Surfactant System Vanadium (IV)-Chlorophosphonazo III-CTAB-Emulsifier OP and Its Application". Journal of Zhejiang of Technology, 1, 1991, p. 54-59.*

Medda et al. "The vanadate complex of the calcium-transport ATPase of the sarcoplasmic reticulum, its formation and dissociation". European Journal of Biochemistry, 1983, 137(1-2), 7-14.*

* cited by examiner

*Primary Examiner*—Jill Warden
*Assistant Examiner*—Monique Mirabeau
(74) *Attorney, Agent, or Firm*—Kratz, Quintos & Hanson, LLP

(57) ABSTRACT

A method for determination of calcium in a sample derived from a living body, by the reaction of calcium in the sample with Chlorophosphonazo-III or a compound analogous thereto in the presence of vanadate ions, followed by determination of calcium in the sample on the basis of an optical change caused by the reaction product, is excellent in various respects as follows: it is free from the problem of absorption of carbonic acid gas caused by a high pH; it is free from the problem of use of a toxic reagent containing arsenic; it makes it possible to subject a large number of samples to determination in a short time because it can be applied to an autoanalyzer; and it permits determination in a wide range because of low sample blank values.

8 Claims, No Drawings

REAGENT FOR DETERMINATION OF CALCIUM AND DETERMINATION METHOD

BACKGROUND OF THE INVENTION

1. Field of the Invention

The present invention relates to a reagent for determination of calcium and a determination method. More particularly, it relates to an improved reagent for determination of calcium and an improved determination method which permit accurate determination of calcium in a sample derived from a living body, such as a blood sample (e.g. whole blood, plasma or serum) or an aqueous liquid sample derived from a living body (e.g. cerebrospinal fluid, lymph, salivary juice or urine) and are especially useful for clinical diagnoses. Furthermore, the present invention relates to a blank-controlling agent for chelating and color-producing agent used in the determination of metal ions by the reaction of a chelating and color-producing agent with the metal ions.

2. Description of the Related Art

As a method for quantitative analysis for calcium ions in a sample, a colorimetry method using a chelating and color-producing agent is commonly practiced for clinical laboratory tests and in the general chemical analysis fields. As the chelating and color-producing agent, o-cresolphthalein complexone (o-CPC) is mainly used which has a pH value most suitable for coloration in an alkaline pH range in which its bonding to calcium for the formation of a chelate is stable, in particular, a high pH range of pH 10 or more, as disclosed in, for example, JP-A-54-36996. There is also known a reagent obtained by incorporating 8-hydroxyquinoline into Arsenazo-III used as a chelating and color-producing agent, to stabilize this agent, as disclosed in Japanese Patent Application Kohyo No. 06-505560. In addition, there is also known an integral-type multi-layer analyzing element for calcium analysis obtained by the use of Chlorophosphonazo-III as a chelating and color-producing agent and having a determination range expanded by the use of light-scattering particles, as disclosed in JP-A-06-50976. Moreover, JP-A-04-120464 discloses that calcium and magnesium can be quantified at the same time by using Chlorophosphonazo-III as a chelating and color-producing agent.

However, each of conventional reagents for calcium determination obtained by using a chelating and color-producing agent leaves something to be improved. For example, a reagent for determination obtained by using o-CPC should be improved because it has a pH of 10 or more. That is, since this reagent has a high pH, its pH is remarkably lowered at the time of use by absorption of carbonic acid gas in the air. Moreover, when the reagent is stored in the form of a solution for a long period of time, its pH is lowered, so that measured values become inaccurate in some cases. On the other hand, the reagent for calcium determination obtained by using Arsenazo-III is advantageous in having a lower pH as compared with a method using o-CPC, but Arsenazo-III is an organic arsenic compound and hence there is no denying the problem of environmental pollution caused by the disposal of the reagent. In the case of Chlorophosphonazo-III, a pH range most suitable for its color change is weakly acidic and Chlorophosphonazo-III is a reagent containing no arsenic. Therefore, Chlorophosphonazo-III is advantageous with respect to problems caused by a high pH and toxicity. The integral-type multi-layer analyzing element for calcium analysis, however, is not a liquid reagent and does not make it possible to subject a large number of samples to determination in a short time. In addition, in the simultaneous qualification of magnesium and calcium, Chlorophosphonazo-III is added to a sample to bond both magnesium and calcium thereto and cause coloration, and then EGTA is added to dissociate calcium therefrom and cause tone reduction, and calcium is quantified on the basis of the degree of the tone reduction. Since Chlorophosphonazo-III gives high blank values, it limits a range where the determination is possible.

That is, although several reagents for calcium determination obtained by using a chelating and color-producing agent have been proposed, a reagent has not yet been proposed which can solve all of the various problems, i.e., the problem of carbonic acid gas absorption caused by a high pH, the problem of use of the toxic arsenic compound, the problem of the impossibility of determination for a large number of samples in a short time, and the problem of high blank values and hence a narrow range where the determination is possible.

SUMMARY OF THE INVENTION

Accordingly, a subject of the present invention is to solve the problems described above and provide a reagent that is excellent in storage stability, is free from the problem of environmental pollution, and permits accurate calcium determination in the form of a solution.

The present inventors investigated reagents for calcium determination involving such problems and consequently found that unexpectedly, a solution of Chlorophosphonazo-III greatly reduces blank values in the presence of vanadate ions. As a result, it was found that in the determination of calcium, by using Chlorophosphonazo-III or a compound analogous thereto as a chelating and color-producing agent in a sufficient amount for the reaction with calcium in a body fluid and using vanadate ions in combination therewith, the problem of the narrow determination range and the problem of the low precision of determination due to high blank values, which are the biggest disadvantages of the employment of Chlorophosphonazo-III or the analogous compound, can be solved at a stroke, so that the range of determination of a species to be detected is expanded and that the determination can be carried out with high precision. The present invention is based on this finding.

Therefore, the present invention provides a reagent for determination of calcium which comprises vanadate ions and Chlorophosphonazo-III or a compound analogous thereto.

In addition, the present invention provides a method for determination of calcium in a sample which is characterized by reacting calcium in the sample with Chlorophosphonazo-III or a compound analogous thereto in the presence of vanadate ions, and determining calcium in the sample on the basis of an optical change caused by the reaction product.

Furthermore, the present invention provides a blank-controlling agent for chelating and color-producing agent used in the determination of metal ions on the basis of an optical change caused by the reaction of a chelating and color-producing agent with the metal ions, which comprises vanadate ions capable of suppressing the coloration of the chelating and color-producing agent itself, as an active ingredient.

The reagent for determination of calcium and determination method of the present invention are excellent in various respects as follows: they are free from the problem of absorption of carbonic acid gas caused by a high pH; they are free from the problem of use of a toxic reagent containing arsenic; they make it possible to subject a large number of samples to determination in a short time because they can be employed in an autoanalyzer; and they permit determination in a wide range because of low sample blank values.

DESCRIPTION OF THE PREFERRED EMBODIMENTS

The reagent for determination of calcium of the present invention is characterized by comprising vanadate ions and Chlorophosphonazo-III or a compound analogous thereto.

In the reagent for determination of calcium of the present invention, disodium 2,7-bis[(4-chloro-2-phosphonophenyl)azo]-4,5-dihydroxy-2,7-naphthalenedisulfonate (Chlorophosphonazo-III) [1914-99-4] or a compound analogous thereto is used as an indicator capable of binding to calcium ions to undergo an optically detectable change. Chlorophosphonazo-III is a compound having the following structural formula, or a salt thereof. Sodium salt is preferable as the salt.

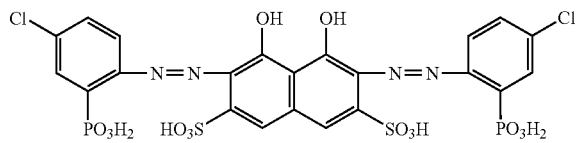

The analogous compound is not particularly limited so long as it is, for example, a compound having the following skeleton or a salt thereof, which binds to calcium ions to develop a color.

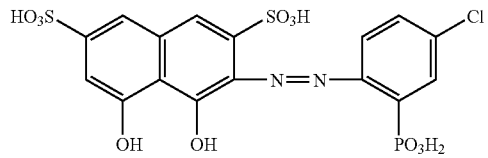

Of such compounds, heretofore known compounds include disodium 3-[(4-chloro-2-phosphonophenyl)azo]-4,5-dihydroxy-2,7-naphthalenedisulfonate (Chlorophosphonazo-I) [1938-82-5], disodium 3-3-[(acetylphenyl)azo]-6-[(4-chloro-2-phosphonophenyl)azo]-4,5-dihydroxy-2,7-naphthalenedisulfonate (Chlorophosphonazo-mA) [86167-87-5], and salts thereof. Sodium salts are preferable as the salts.

In the present invention, vanadate ions are used together with Chlorophosphonazo-III or such an analogous compound. Vanadate ions can act effectively on Chlorophosphonazo-III or the analogous compound as a blank-controlling agent, namely, they can act effectively so as to suppress the coloration of Chlorophosphonazo-III itself or the analogous compound itself.

Although the vanadate ions used in the reagent for determination of calcium of the present invention are not particularly limited so long as they are usable for the object of the present invention, those containing pentavalent vanadium, such as $VO_3^-$, $VO_4^{3-}$ and the like are preferable. When these vanadate ions are used in practice, it is preferable from the viewpoint of solubility to use them in the form of a salt such as a salt with an alkali metal (e.g. lithium, sodium or potassium), an ammonium salt or the like.

Although any sample may be used as a sample to be subjected to determination by the use of the reagent for determination of calcium of the present invention, a sample derived from a living body is suitable, namely, the reagent is suitable for the determination of calcium in a sample derived from a living body. The sample derived from a living body includes, for example, blood samples (e.g. whole blood, plasma and serum), aqueous liquid samples derived from living bodies (e.g. cerebrospinal fluid, lymph, salivary juice and urine), and diluents thereof. In the present invention, even when a sample such as serum containing a chelating agent such as EDTA is used as the sample derived from a living body, calcium in the sample can be accurately determined. When such serum is used, a method using o-CPC does not permit accurate determination. Therefore, the reagent for determination of calcium of the present invention is advantageous also in being usable in the case of various samples.

The reagent for determination of calcium of the present invention is not particularly limited so long as it is a reagent comprising vanadate ions and Chlorophosphonazo-III or a compound analogous thereto. As said reagent, a reagent comprising two reagents (hereinafter referred to as "two-reagent system" in some cases) is preferable because it is usable in a biochemical autoanalyzer. In the present invention, in the case of the two-reagent system, its first reagent preferably contains a generally used buffer (e.g. sodium acetate) and a surfactant. The second reagent of the two-reagent system contains Chlorophosphonazo-III as an essential constituent, preferably contains a generally used buffer (e.g. sodium acetate) and a surfactant, and may contain a salt (e.g. sodium chloride) and an antiseptic (e.g. sodium azide). In the case of the two-reagent system, vanadate ions are preferably incorporated into the second reagent like Chlorophosphonazo-III from the viewpoint of the stability of the reagent.

The reagent for determination of calcium of the present invention is preferably adjusted so that the pH of a liquid for the reaction of a sample with Chlorophosphonazo-III, for example, the pH of a liquid obtained by combining a first reagent and a second reagent in the case where the reagent of the present invention is composed of these two reagents, may be preferably 3.5 to 7.5, more preferably 4.5 to 6.5, especially preferably 4.8 to 6.2. When the pH of this liquid is less than 3.5, a protein in a sample and Chlorophosphonazo-III tend to bind to each other in the determination of calcium, so that it is difficult to determine calcium accurately. When the pH of the liquid is more than 7.5, high reagent blank values are obtained or the influence of magnesium is exerted. Therefore, accurate determination is impossible in some cases. It is preferable that the first reagent and second reagent of the two-reagent system independently have a pH of 2.0 to 9.0. Also in this case, the pH of a liquid obtained by combining the first reagent and the second reagent is preferably 3.5 to 7.5. The second reagent more preferably has a pH of 7.5 to 9.0, in particular, a pH of 7.7 to 8.5, from the viewpoint of the solubility of Chlorophosphonazo-III and vanadate ions.

When calcium is determined in the present invention by the use of the reagent for determination composed of two reagents, i.e., a first reagent and a second reagent, the volume ratio among a sample used, the first reagent and the second reagent is preferably, for example, 1:(10 to 100):(2 to 25) though it is varied depending on an autoanalyzer used and the like.

Next, the determination method of the present invention is explained below. The method for determination of calcium of the present invention is characterized by reacting calcium in a sample with Chlorophosphonazo-III or a compound analogous thereto in the presence of vanadate ions.

In the present invention, as to the concentration at the time of reaction with calcium (hereinafter referred to as "final concentration" in some cases), the final concentration of Chlorophosphonazo-III is preferably, for example, 0.01 to 10 mM, more preferably 0.05 to 2 mM, especially preferably 0.1 to 0.7 mM, though it is adjusted depending on the amount of a sample used, and the like. When the concentration is insufficient, Chlorophosphonazo-III does not easily bind to calcium in some cases. When the concentration is too high, high blank values are obtained, so that accurate determination is difficult.

As to the concentration (mM) of vanadate ions, their final concentration is preferably 1 to 300 times, more preferably 3 to 200 times, especially preferably 5 to 100 times, that of Chlorophosphonazo-III. When the concentration of vanadate ions is too low, high blank values are obtained in some cases.

There is described below a specific example of determination of calcium in plasma by the use of the present inventive reagent for determination of calcium composed of two reagents, i.e., a first reagent and a second reagent.

The first reagent containing a buffer and a sample derived from a living body are mixed at a definite temperature, preferably 25 to 37° C., for a definite time, for example, 5 minutes. To the resulting liquid is added the second reagent containing Chlorophosphonazo-III and vanadate ions, and they are mixed at a definite temperature, preferably 25 to 37° C., for a definite time, for example, 5 minutes to carry out the coloration reaction of calcium in the sample with Chlorophosphonazo-III. The absorbance values of the reaction solution before and after the coloration due to Chlorophosphonazo-III are measured and an absorbance change caused by the coloration is calculated. The concentration of calcium in the sample derived from a living body may be measured, for example, by the comparison of the absorbance change with a calibration curve. The absorbance may be measured usually at 660 nm.

When calcium is determined by the use of the reagent for determination of the present invention, a biochemical autoanalyzer such as Hitachi Model 7150, Hitachi Model 7170S, or the like may be used.

Next, the blank-controlling agent for chelating and color-producing agent of the present invention is explained below. The blank-controlling agent of the present invention is characterized by containing vanadate ions.

Chlorophosphonazo-III or the like binds to various metal ions such as calcium ions and hence permits determination of the metal ions. A solution of Chlorophosphonazo-III, however, is a highly colored solution in itself and hence gives high sample blank values in the determination of metal ions. As a result, there has been a problem of a narrow metal ions determination range. Vanadate ions are effective in suppressing the coloration of a Chlorophosphonazo-III solution to control blank values. Therefore, when metal ions such as calcium ions are determined by using Chlorophosphonazo-III or a compound analogous thereto, vanadate ions are useful as a blank-controlling agent for Chlorophosphonazo-III or the analogous compound.

The present inventive blank-controlling agent comprising vanadate ions as an active ingredient may be used also when metal ions such as ions of magnesium, barium, calcium or the like are determined by using a chelating and color-producing agent other than Chlorophosphonazo-III or a compound analogous thereto, such as Dimethylsulfonazo-III, Arsenazo-I or the like. To use the blank-controlling agent of the present invention in practice, it is sufficient that vanadate ions are made present at the time of the reaction of the chelating and color-producing agent with metal ions as in the above-mentioned method for determination of calcium of the present invention.

EXAMPLE 1 AND COMPARATIVE EXAMPLES 1 TO 4

Calcium Determination Using Chlorophosphonazo-III in the Presence of Vanadate Ions 1. Method An experiment was carried out in order to judge whether calcium in a sample derived from a living body could be accurately determined with Chlorophosphonazo-III (referred to as CPZ-3 in some cases) in the presence of vanadate ions. The determination result obtained in the presence of vanadate ions was compared with those obtained in the presence of each of sodium tungstate, manganese(II) sulfate, copper(II) sulfate and no metal ions. As a sample, a first reagent and a second reagent, the following were used.

Sample

A sample derived from a living body and containing calcium in an amount of 7.9 mg/dL (a value measured by a method using o-CPC).

| First reagent | |
| --- | --- |
| Sodium dihydrogenphosphate | 50 mM pH 6.0 |
| Surfactant | 1.0% |
| Second reagent | |
| Chlorophosphonazo-III (CPZ-3) | 1.25 mM |
| Sodium chloride | 150 mM |
| Ammonium vanadate | 40 mM |
| Surfactant | 1.0% |

Comparative examples were as follows. In Comparative Example 1, no metal ions were added. In Comparative Example 2, 40 mM of sodium tungstate was added. In Comparative Example 3, 40 mM of manganese(II) sulfate was added. In Comparative Example 4, 40 mM of copper(II) sulfate was added.

A determination method was as follows. Using an Autoanalyzer Hitachi Model 7170S, 2.5 μL of the sample and 200 μL of the first reagent were mixed at 37° C. for 5 minutes, and to the resulting liquid was added 50 μL of the second reagent and the coloration reaction was carried out at the same temperature for 5 minutes. The difference of absorbance before and after the coloration reaction was measured at a dominant wavelength of 660 nm. The concentration of calcium was calculated by the following equation 1:

$$\text{Ca concentration (mg/dL)} = \frac{(E_{Abs} - E_{Blank})}{E_{STD} - E_{Blank}} \times \text{STD concentration} \qquad \text{Equation 1}$$

$E_{Abs}$: a measured absorbance value
$E_{Blank}$: the absorbance of a blank solution
$E_{STD}$: the absorbance of a standard solution
STD concentration: the concentration of the standard solution

2. Results

Table 1 shows the results obtained.

TABLE 1

|  | Example 1 | Comparative Example 1 | Comparative Example 2 | Comparative Example 3 | Comparative Example 4 |
|---|---|---|---|---|---|
| Metal added | $VO_3^-$ | None | $WO_4^{2-}$ | $Mn^{2+}$ | $Cu^{2+}$ |
| $E_{Blank}$ | 6620 | 22115 | 34496 | 43851 | 16050 |
| $E_{STD}$ | 13585 | 27104 | 36076 | 44294 | 15444 |
| Measured value | 7.8 | 9.4 | 10.8 | 1.2 | 0 |

From the results shown in Table 1, it was found that in the presence of vanadate ions, calcium in the sample derived from a living body can be accurately determined by its reaction with CPZ-3. It was also found that calcium cannot be accurately determined when the determination is carried out by adding no metal or in the presence of a metal other than vanadium. In the presence of vanadate ions, CPZ-3 forms a chelate complex with vanadate ions to change in absorbance near 660 nm. The thus formed chelate complex of CPZ-3 and vanadate ions blocks a nonspecific reaction of CPZ-3 with a protein. Moreover, since CPZ-3 has a higher specificity for Ca than for vanadate ions, CPZ-3 makes it possible to determine Ca accurately in the presence of vanadate ions. On the other hand, when no metal ions were added, the nonspecific reaction of CPZ-3 with a protein in the sample derived from a living body occurred in the determination of calcium in the sample derived from a living body, so that absorbance was increased to cause positive errors. In the presence of any of the other added metals, a chelate complex of CPZ-3 and the added metal inhibited the reaction of Ca with CPZ-3, so that an accurate calcium level could not be calculated. These facts suggest that the strength of bonding of CPZ-3 to each component is as follows:

$$Cu^{2+} > Ca^{2+} > VO_3^- > protein > WO_4^{2-}, Mn^{2+}$$

EXAMPLE 2

Investigation of pH in a Reaction Solution

Calcium in serum was determined by adjusting a liquid under chelation reaction in the presence of vanadate ions to each of various pH values (pH 4.0, 5.0 and 6.0). As a sample, a first reagent and a second reagent, the following were used.

Sample

A sample derived from a living body and containing calcium in an amount of 7.6 mg/dL.

| First reagent | |
|---|---|
| Glycine | 100 mM (in the case of pH 4.0) or |
| sodium acetate | 100 mM (in the case of pH 5.0 or 6.0) |
| Surfactant | 1.0% |
| Second reagent | |
| CPZ-3 | 1.25 mM |
| Sodium chloride | 150 mM |
| Ammonium vanadate | 40 mM |
| Surfactant | 1.0% |

Table 2 shows the results obtained.

TABLE 2

| pH of reagent (pH at reaction) | pH 4.0 | pH 5.0 | pH 6.0 |
|---|---|---|---|
| $E_{Blank}$ | 3091 | 3206 | 4034 |
| $E_{STD}$ | 8714 | 7152 | 9977 |
| Measured value | 7.08 | 7.56 | 7.50 |

From the results shown in Table 2, it was found that carrying out the reaction at, in particular, pH 5.0 or 6.0 is especially preferable for the determination of calcium.

EXAMPLE 3 AND COMPARATIVE EXAMPLES 5 TO 7

Determination of Calcium in a Sample Derived From a Living Body and Containing EDTA An experiment was carried out in order to judge whether calcium in a sample derived from a living body and containing EDTA (a chelating agent) could be accurately determined in the presence of the vanadate ions by its reaction with CPZ-3, a chelating and color-producing agent. In Comparative Example 5, the determination was carried out in the presence of tungstate ions. In Comparative Example 6, the determination was carried out in the absence of metal ions added. As Comparative Example 7, a method using o-cresolphthalein complexone (o-CPC) and no metal ions added was examined which has been a general method for determination of calcium. The compositions of a first reagent and a second reagent for determination of calcium were as follows:

Sample

A sample derived from a living body and containing EDTA (0, 7.5 or 15 mM) and calcium in an amount of 7.6 mg/dL.

| First reagent | |
|---|---|
| Sodium dihydrogenphosphate | 50 mM pH 5.0 |
| Surfactant | 1.0% |
| Second reagent | |
| CPZ-3 | 1.25 mM |
| Sodium chloride | 150 mM |
| Metal ions of each kind | 40 mM |
| Surfactant | 1.0% |

Table 3 shows the results obtained, i.e., calcium measured values and relative values [(measured value×100)/actual amount].

TABLE 3

| | Measurement of calcium concentration (actual amount: 7.6 mg/dL) by addition of EDTA | | | |
|---|---|---|---|---|
| EDTA in sample | Example 3 | Comparative Example 6 (no addition of $VO_3^-$) | Comparative Example 5 (in the presence of $WO_4^{2-}$) | Comparative Example 7 (o-CPC method) |
| 0 mM | 7.48 (98%) | 9.48 (124%) | 10.76 (141%) | 7.6 (100%) |
| 7.5 mM | 7.43 (98%) | 6.63 (87%) | 9.13 (120%) | 0 (0%) |
| 15 mM | 7.45 (98%) | 5.18 (68%) | 8.18 (108%) | 0 (0%) |

It was found that as shown in Table 3, in the presence of vanadate ions, calcium in the sample derived from a living body and containing EDTA can be accurately determined by its reaction with CPZ-3. On the other hand, it was found that in the presence of tungstate ions in place of vanadate ions, calcium cannot be accurately determined. In addition, when no vanadate ions were added, calcium could not be determined by a method using CPZ-3 and the method using o-CPC (a conventional method).

The reagent for determination of calcium and determination method of the present invention have the following advantages: the reagent is stable even when stored for a long period of time and does not involve a problem of toxicity, and the reagent and the method permit accurate and rapid determination of calcium in a large number of samples and are very effective in the field of diagnostic drugs for clinical laboratory test.

The invention claimed is:

1. A method for determination of calcium in a sample, characterized by reacting calcium in the sample with Chlorophosphonazo-III or a compound analogous thereto in the presence of vanadate ions, and determining calcium in the sample on the basis of an optical change caused by the reaction product.

2. A determination method according to claim 1, wherein the sample is a sample derived from a living body which may contain a chelating agent.

3. A determination method according to claim 2, wherein the pH at the reaction of calcium in the sample with Chlorophosphonazo-III or a compound analogous thereto is 3.5 to 7.5.

4. A determination method according to claim 1, wherein the pH at the reaction of calcium in the sample with Chlorophosphonazo-III or a compound analogous thereto is 3.5 to 7.5.

5. A reagent for determination of calcium, which is a two-reagent system composed of a first reagent comprising a buffer and optionally a surfactant, and a second reagent comprising vanadate ions and Chlorophosphonazo-III or a compound analogous thereto.

6. A reagent for determination of calcium according to claim 5, which is adjusted so that the pH of a liquid obtained by combining the first reagent and the second reagent may be 3.5 to 7.5.

7. A reagent for determination of calcium in a sample derived from a living body which may contain a chelating agent, which is a two-reagent system composed of a first reagent comprising a buffer and optionally a surfactant, and a second reagent comprising vanadate ions and Chlorophosphonazo-III or a compound analogous thereto.

8. A reagent for determination of calcium according to claim 7, which is adjusted so that the pH of a liquid obtained by combining the first reagent and the second reagent may be 3.5 to 7.5.

* * * * *